(12) United States Patent
Kindlein et al.

(10) Patent No.: US 8,130,384 B2
(45) Date of Patent: Mar. 6, 2012

(54) APPARATUS AND METHOD FOR THE REPRESENTATION OF AN AREA ON THE SURFACE OF A PATIENT'S BODY

(75) Inventors: Johann Kindlein, Adendorf (DE); Tim Thurn, Lueneburg (DE)

(73) Assignee: LAP GmbH Laser Applikationen, Luneburg (DE)

( * ) Notice: Subject to any disclaimer, the term of this patent is extended or adjusted under 35 U.S.C. 154(b) by 77 days.

(21) Appl. No.: 12/704,979

(22) Filed: Feb. 12, 2010

(65) Prior Publication Data

US 2010/0208274 A1 Aug. 19, 2010

Related U.S. Application Data

(63) Continuation-in-part of application No. 12/132,874, filed on Jun. 4, 2008, now Pat. No. 7,697,147.

(30) Foreign Application Priority Data

Sep. 2, 2009 (EP) .................................... 09011262

(51) Int. Cl.
*G01B 11/30* (2006.01)
(52) U.S. Cl. ....................................... 356/608; 356/601
(58) Field of Classification Search .......... 356/600–608, 356/614, 620–623; 250/559.24, 221, 559.4, 250/559.29, 559.3, 370.08–370.09, 370.1; 378/62–65
See application file for complete search history.

(56) References Cited

U.S. PATENT DOCUMENTS

| | | | |
|---|---|---|---|
| 3,625,618 A | 12/1971 | Bickel | |
| 5,690,107 A | 11/1997 | Hofmann | |
| 6,088,106 A | 7/2000 | Rockseisen | |
| 6,314,311 B1 | 11/2001 | Williams et al. | |
| 2006/0215813 A1 * | 9/2006 | Scherch et al. | 378/65 |

FOREIGN PATENT DOCUMENTS

| | | |
|---|---|---|
| DE | 44 18 216 A1 | 11/1995 |
| DE | 44 21 315 A1 | 12/1995 |
| DE | 195 24 951 A1 | 1/1997 |
| EP | 2 098 169 A2 | 2/2009 |
| WO | 2009011643 A1 | 1/2009 |

* cited by examiner

*Primary Examiner* — Tri T Ton
(74) *Attorney, Agent, or Firm* — Vidas, Arrett & Steinkraus, P.A.

(57) ABSTRACT

The invention is related to an apparatus for the representation of a geometrical figure on the surface of a patient's body that is situated on a support, comprising at least one projection device, by which a given geometrical figure can be projected onto the three-dimensional surface of the patient's body, at least one control device and at least one optical sensor device, by which the geometrical figure projected onto the surface of the patient's body can be acquired and the acquired data can be supplied to the control device, wherein the control device is realized to determine the three-dimensional coordinates of the geometrical figure projected onto the patient's body from the data acquired by the sensor device, and wherein the control device is realized to compare the determined three-dimensional coordinates of the geometrical figure projected onto the patient's body with desired three-dimensional coordinates.

17 Claims, 2 Drawing Sheets

Figure 1:
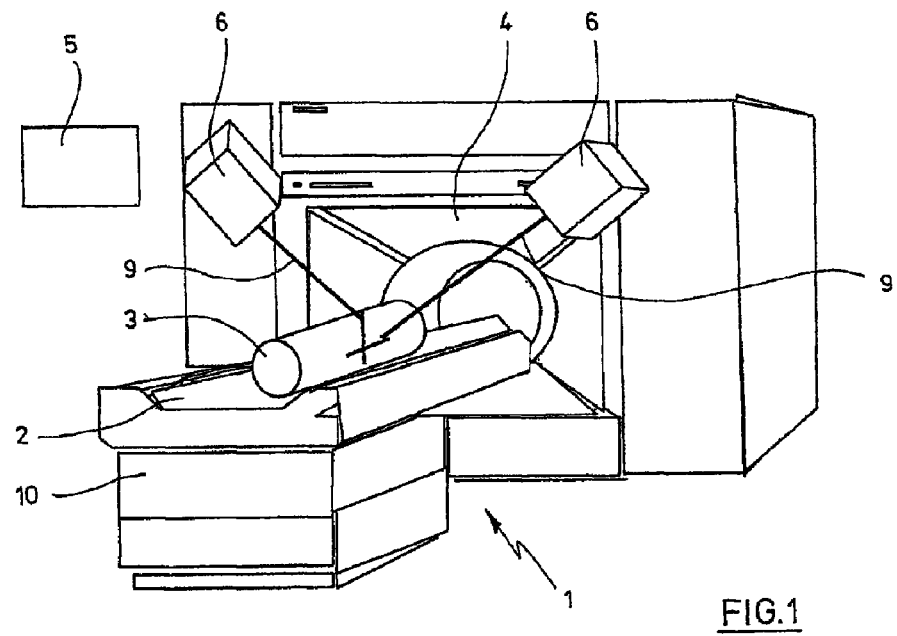

APPARATUS AND METHOD FOR THE REPRESENTATION OF AN AREA ON THE SURFACE OF A PATIENT'S BODY

CROSS-REFERENCE TO RELATED APPLICATIONS

This application is a Continuation In Part application from application Ser. No. 12/132,874 filed Jun. 4, 2008 now U.S. Pat. No. 7,697,147 the contents of which is hereby incorporated by reference.

STATEMENT REGARDING FEDERALLY SPONSORED RESEARCH

Not applicable.

BACKGROUND OF THE INVENTION

The present invention is related to an apparatus and a method for the representation of a geometrical figure on the surface of a patient's body that is situated on a support, and relates to the field of radiation therapy with ionising radiation for treating cancer. In this, usually plural rays from different directions are directed towards the body to be treated, so that they intersect in an isocentre. Here acts the summed-up radiation dose of the different ionising rays directed to the isocentre. In this way, the adverse effect to the surrounding tissue is minimised.

A computer tomography (CT) mapping of the patient positioned and fixed on a support, like a treatment table, is usually established as the first step of a radiation therapy. Based on this mapping, a 3D-model of the patient is made and the tumour to be treated is localised and an irradiation plan is set up. This comprises contouring the target volumes as well as the calculation of the dose for the irradiation, and in this the determination of the number and location of the radiation areas of the irradiation machine in particular, so that the tumour is irradiated as desired.

After the mapping of the patient, the patient is no more on the support. Furthermore, a plurality of irradiation dates (usually up to 30 fractions) takes usually place in the frame of a subsequent radiation therapy. Therefore, a transfer of the radiation areas calculated on the basis of the established 3D-model of the patient to the real patient is repeatedly necessary. This step is also called "simulation". In particular, the patient must be reproducibly laid on the treatment table such as he/she lay when the CT mapping was established.

In order to do this, it is known to perform a positioning of the patient by means of 3D radiography ("Cone Beam"), wherein bones of the patient constitute the reference points for an alignment of the patient, for instance. The advantage of this method is a high accuracy. In addition, no reference marks or the like have to be affixed on the patient's skin. The disadvantage of this method is a high x-ray radiation dose for the patient, because the x-ray positioning is required before each treatment fraction. That is to say, in the frame of a radiation therapy, this may usually take place up to 30 times. This radiation dose applied to the body in a great volume can induce a new cancer again in the long term, in younger patients in particular.

According to a known alternative method, the patient can be positioned on the support by means of three reference points on its skin, which are formed by suitable retro reflectors, for instance. Such a method is known from DE 44 18 216 A1, the entire contents of which is incorporated herein by reference. After performing the irradiation planning, the intersection points of the irradiation areas with the surface of the skin which are necessary for the desired irradiation are calculated. The intersection points are then at hand in the form of a 3D coordinate table. After newly positioning the patient on the basis of the three reference marks, the coordinates from the table can then be represented on the body surface of the patient one after the other with a laser system. The approach to the coordinates can be controlled by an operator, for instance by an infrared remote control. The respective points represented by the laser are then manually drawn in on the skin of the patient, with a pencil for instance. The desired intersection area for the irradiation results by connecting the points.

Such a method is known from DE 44 21 315 A1 or DE 195 24 951 A1 the entire contents of which is incorporated herein by reference. The laser device used for this consists of five motor movable lasers in particular, wherein two lasers adjustable in the height direct a horizontal line along the treatment table to the patient, at the right and at the left side from the treatment table, respectively. The remaining three lasers are mounted in a plate which is situated above the treatment table, a CT table for instance. In this, one laser is movable transversely to the table's long side direction and directs a line along the table to the patient. The two remaining lasers in the plate are coupled with each other and direct a common line to the patient, transversely to the table's alongside. By the coupling of two lasers, even such coordinates can be represented on the skin of the patient which otherwise would be shaded below the transverse diameter of the patient. With the described system, it is possible to approach almost arbitrary coordinates on the skin of the patient, wherein one coordinate is always indicated by a cross of two laser lines. Such a laser system is offered by the applicant under the name "Dorado CT4".

However, the described method is relatively time-consuming and therefore expensive, because usage time in the CT-room is very expensive. In addition to this, manual drawing in the points is not always sufficiently accurate, depending on the adiposity of the patient in particular. In particular, skin marks can shift. Therefore, marks of the intersection areas on the skin are performed only partially in practice. Correspondingly, the correct irradiation of the patient is not always ensured in a sufficiently accurate way.

Moreover, there is a problem in that the position of the patient between the irradiation planning and in particular in a mapping of the patient's body performed in this on the one hand, and a later irradiation date on the other hand, is inevitably not always identical, in spite of the utilisation of identical positioning aids on the treatment table. The procedures for reproducible positioning of the patient explained above are relatively sumptuous and do not always achieve the necessary accuracy in practice.

The simulation is not only an assignment of the irradiation plan to the patient, but also an important element in the context of the quality assurance. The irradiation plan is checked for its plausibility for the last time before the therapy and it is determined whether the ray areas can be reproducibly adjusted to the desired planned target volume.

Based on the clarified state of the art, the present invention is based on the objective to provide an apparatus and a method of the kind indicated in the beginning, by which a reproducible, accurate positioning of the patient is possible in a reliable manner.

BRIEF SUMMARY OF THE INVENTION

On the one hand, the present invention achieves the objective by an apparatus for the representation of a geometrical figure on the surface of a patient's body that is situated on a support, comprising: at least one projection device, by which a given geometrical figure can be projected onto the three-dimensional surface of the patient's body, at least one control device and at least one optical sensor device, by which the geometrical figure projected onto the surface of the patient's body can be acquired and the acquired data can be supplied to the control device, wherein the control device is realized to determine the three-dimensional coordinates of the geometrical figure projected onto the patient's body from the data acquired by the sensor device, and wherein the control device is realized to compare the determined three-dimensional coordinates of the geometrical figure projected onto the patient's body with desired three-dimensional coordinates.

On the other hand, the present invention achieves the objective by a method for the representation of a geometrical figure on the surface of a patient's body that is situated on a support, comprising the steps: a given geometrical figure is projected onto the three-dimensional surface of the patient's body by a projection device, the geometrical figure projected onto the surface of the patient's body is acquired by means of an optical sensor device and the acquired data are supplied to the control device, wherein the control device determines the three-dimensional coordinates of the geometrical figure projected onto the patient's body from the data acquired by the sensor device, the determined three-dimensional coordinates of the geometrical figure projected onto the patient's body are compared with desired three-dimensional coordinates by the control device.

In this, the given geometrical form can be selected such that the envisioned body region is irradiated by the radiation in the manner desired and calculated in the context of the irradiation planning. Thus, the geometrical figure can be a desired intersection area of a radiation area generated by an irradiation apparatus with the body surface of the patient. The figure is then depending on the form of a multi leaf collimator of an irradiation machine, a linear accelerator for instance, and/or the position of the isocentre of a tumour to be treated. Plural geometrical forms can be represented also, in case that plural rays are used for the treatment which must intersect in an isocentre situated in the body of the patient.

According to the present invention, a certain geometrical figure is given, which is then projected onto the surface of the patient's body by means of the projection device. The given geometrical form can be a circle, a rectangle, a cross or the like, e.g. The geometrical figure projected onto the real patient's body is acquired by the sensor device. For this purpose, the sensor device may have one or plural cameras, like CCD- or CMOS cameras e.g. When using plural cameras, the three-dimensional coordinates can be determined more accurately, because the geometrical figure is mapped from different angles of view. The measurement data of the sensor device are supplied to the control device, and the latter determines the three-dimensional coordinates of the geometrical figure on the patient's body from the same in a per se known manner. By the control device, the three-dimensional coordinates determined in this way are then compared with the desired coordinates of the geometrical figure provided beforehand. These desired coordinates are those coordinates of the geometrical figure on the surface of the patient's body which is situated on the support that would result if the patient were positioned on the support in a previously established reference position, and the geometrical figure would be projected by the projection device onto the patient's body situated in the reference position in the same way as during the projection onto the real patient's body. The reference position is that position which the body has to take on for the irradiation. That is to say, if the determined coordinates deviate from the desired coordinates, the patient's body is not in the correct position. As already explained, the patient is positioned on the support, which may be a treatment table e.g., by means of suitable positioning devices or positioning aids, respectively. As also already explained, even when using identical positioning aids, it cannot be ensured that the patient always takes on the same position. This can be taken into account or be compensated for, respectively, based on the comparison of the coordinates according to the present invention, in a manner that will be still explained below. Thus, according to the present invention, a direct correlation is produced between the virtual patient in the computer, based on a CT image for instance, and the real patient.

The apparatus according to the present invention can be arranged in the treatment room with the irradiation machine, a linear accelerator (LINAC) for instance, in the CT room with a CT machine or in a separate room. An irradiation machine or a CT might also be envisioned for the apparatus in a corresponding manner. In particular, the desired coordinates of the geometrical figure provided by the control device can be established on the basis of a CT mapping of the patient in a manner that will still be explained below. Furthermore, the apparatus can feature a computer system with a graphic image representation and software (algorithms) for the virtual simulation of the irradiation of a patient on the basis of CT mappings with interfaces for the transmission of image data, irradiation data, irradiation area contours and so on. This computer system may be a part of the control device. The different devices of the apparatus can be connected via a local network. The exchange of the data can proceed in a particularly simple manner via the Digital Imaging and Communications in Medicine (DICOM and DICOM RT) standard. For instance, the system can grant different functionalities and rights in different rooms. For purposes of quality control, all the data files can be filed in a server file.

Even marking of the patient with a pencil or the like along the geometrical figure projected onto body surface is possible, but not necessarily required. As explained, the geometrical figure can be a desired intersection area of a radiation area generated by an irradiation machine with the body surface of the patient. On the basis of the projection, the represented desired intersection area can be marked on the skin in a particularly simple manner, drawn in with a pencil or the like, for instance. In this case, the apparatus has not to be arranged in the irradiation room. Instead, the simulation may take place in a separate room, whose use is less expensive than that of the irradiation or CT room. In addition, the irradiation or CT room has not to be rebuilt by the installation of the apparatus of the invention in this case. After marking the patient, a light area simulating the treatment area can be directed to the patient in the irradiation room with the irradiation machine and the patient can be aligned such that the mark and the light area are coincident. This may take place manually or automatically, as will be explained in more detail below.

In a particularly practical way, it can be provided that the projection device has at least one light source, at least one laser in particular, wherein the geometrical figure can be projected onto the surface of the patient's body while at least one light beam generated by the light source, at least one laser beam generated by the laser in particular, can be guided along the coordinates sufficiently rapidly, so that the impression of a closed contour along the coordinates results. Thus, by means of a laser projector as the optical system, the points of the geometrical figure are approached one after another. In doing so, the points are approached by the laser beam so rapidly that for a human spectator and also for a camera, a closed contour around the figure appears on the skin. In this, no time-consuming manual approach to coordinates from the table of the irradiation planning is necessary. The use of x-rays that are hazardous for the health is not necessary. Moreover, for instance when the apparatus is arranged in the irradiation room with an irradiation machine, no manual marking of the geometrical figure representing a desired intersection area of the irradiation machine is necessary on the skin of the patient. Instead, during the projection, a light intersection area produced by the irradiation machine and indicating the radiation generated by the machine can be brought into coincidence with the projected desired intersection area for the irradiation. The projection can take place in a particularly simple manner when the projection device has at least two rotatable mirrors, by which a laser beam can be reflected onto the surface of the patient's body and can be guided along the contour of the geometrical figure. For instance, the mirrors may be electrically driven galvanometer mirrors. With this embodiment, a particularly high precision is achieved in the projection.

In order to have the system executable, a calibration of the projection device must be performed by providing calibration coordinates which are addressed by the control device and thus the calibration parameters are determined. At least six points must be addressed. In this, one of the calibration points which is used for calibration lays in the isocentre of a CT-machine or a linear accelerator.

According to a further embodiment, the desired coordinates can be determined or had been determined, respectively, in advance in the frame of an irradiation planning or virtual simulation, in which a virtual representation of at least the surface of the patient's body is produced. As the desired coordinates, those coordinates of the geometrical figure are then given that would result if the projection device would project the geometrical figure onto the virtual patient's body. For instance, a CT mapping of the patient can be produced in the frame of the irradiation planning. From this, a virtual patient's body and in particular a virtual surface of the patient's body can be produced. The three-dimensional coordinates of the virtual body are known, because the arrangement of the mapping device, of a CT device for instance, is known in the respective coordinate system. The position of the body in the irradiation planning serves then as a reference position for the later irradiation for tumour treatment. The projection device is arranged or aligned, respectively, in a defined manner, for instance to the isocentre of an irradiation machine. The relative position of the projection device to the support is also known. The fixedly defined arrangement or alignment, respectively, of the projection device in the projection of the geometrical figure onto the real patient's body is also made the basis of the preliminary irradiation planning. In particular, for the virtual projection of the figure onto the patient's body, the same arrangement of the projection device is presumed that will be present in the later real projection onto the patient's body.

Now, at least those 3D-coordinates of the geometrical figure are determined which would result if the projection device arranged or aligned, respectively, in a defined manner would project the figure onto the virtual body. Of course, the geometrical figure can also be represented virtually on the virtual body. In fact, when the virtual body is mapped, the patient is positioned on the treatment table with the same positioning aids as in the later irradiation. Anyhow, position deviations will result inevitably (as the case may be, even by bodily changes like increase or decrease of weight). Therefore, when the geometrical figure is projected onto the real body by the projection device, there will be a deformation of the figure, and through this a deviation of the coordinates of this figure from those of the virtual figure on the virtual patient's body. According to the present invention, this deviation is detected and can be taken into account, be corrected in particular.

It is also possible to project the geometrical figure (virtually) onto the isocentre of a tumour in the virtual patient. For this purpose, the necessary alignment of the real projection device can be determined and adjusted correspondingly in the later real projection. The virtual geometrical form is then not deformed, for instance, a circle is then a circle also on the surface of the virtual body. Subsequently, the virtual patient with the isocentre of the tumour can be virtually displaced into the isocentre of an irradiation machine used in the later therapy. In this, the geometrical figure is deformed. For instance, a circle becomes an ellipse or the like. The coordinates of this deformed figure can then be used as desired coordinates, so that even the real patient with the isocentre of the tumour is displaced into the isocentre of the irradiation machine. According to the present invention, it is ensured that in an irradiation, the same patient position is made the basis which was present in the irradiation planning and in particular in the mapping of the virtual patient's body. By doing so, one achieves a correct irradiation.

From the comparison of the determined coordinates and the desired coordinates, a displacement vector for the support can be calculated by the control device, in order to bring the determined coordinates into coincidence with the desired coordinates. Furthermore, the support can be movable along one or plural degrees of freedom by means of suitable adjustment drives. In particular, the support can be movable along at least three degrees of freedom, which may be three axes that are aligned orthogonally to each other. However, an adjustability may also be possible along more than three degrees of freedom, for instance in six degrees of freedom, so that a rotation of the table is possible e.g. Then, the control device can control the adjustment drives such that the support is moved according to the calculated displacement vector, the patient situated on the support being displaced into the given reference position as a consequence. The analysing device has a corresponding analysing algorithm for bringing the two 3D contours into overlapping by a dislocation of the support (matching). The parameters for adjusting the support can be transmitted to the adjustment drives automatically or after input by an operator.

The apparatus can have a visualization software, by which the coordinates of the given geometrical figure and the figure resulting from them as well as the desired coordinates and the desired figure resulting from them can be displayed. Preferably, they can be displayed in different views. Then, by a control device, but preferably by an user of the apparatus, both figures can be brought into overlapping in the representation in a particularly simple and convenient way with the visualization software and by preferably iterative movement of the support, based on the representation of the coordinates of the given geometrical figure and of the figure resulting from them, as well as on the desired coordinates and the desired figure resulting from them.

According to a further embodiment, the sensor device can produce a mapping of the geometrical figure several times per second and supply the acquired data to the control device. Also several times per second, the control device can then determine the three-dimensional coordinates of the geometrical figure projected onto the patient's body from the acquired data and compare them with the desired coordinates. In particular, the data captured by the sensor device can be forwarded in real time or nearly real time to the control device, and analysed by the same also in real time or nearly real time. Through this embodiment, a high resolution monitoring of the patient's movement is possible according to the number of the measurements and analyses per second. In particular, monitoring the breathing cycle can be performed when the geometrical figure is projected onto the thorax of the patient, for instance. For instance, the capture and analysis of the geometrical figure can take place more than 10 times, preferably more than 20 times per second. A high resolution (real time or nearly real time) new positioning of the patient can then take place correspondingly, depending on his/her movement, of a movement of the thorax for instance, while the control device calculates the displacement vector several times per second and controls the adjustment drives of the support such that the support is moved according to the calculated displacement vector.

The apparatus can furthermore feature an irradiation machine for generating ionising radiation for the radiation therapy. A light radiation corresponding to the radiation generated by the irradiation machine can be generated by the irradiation machine. The irradiation machine serves for tumour treatment and may be a linear accelerator, for instance. Then it is possible that the control device addresses the irradiation machine several times per second to generate the ionizing radiation always then when the comparison of determined coordinates and desired coordinates takes on a desired value. Thus, a so-called "gating" of the irradiation machine can take place in this embodiment, by activating it only then when the comparison yields the desired value or approaches it at least sufficiently. Of course, upper and lower limit values around a certain value can be given, so that there is a desired value interval. When the comparison value falls into this desired value interval, the irradiation machine is activated, when not it is deactivated. Thus, it can be irradiated always only then when the thorax, and with the same for instance a tumour located in the region of the thorax, is in a certain position of the breathing cycle. That is to say, there is a control of the irradiation machine in real time or nearly real time depending on the patients movement.

According to the present invention, plural laser projection devices, two for instance, may be provided in order to be able to represent the geometrical figure on all the positions of the patient's body. Thus, for instance, at least one projector arranged above the support can be provided at a time on the left and on the right side of the support that accommodates the patient. However, it is also possible that the projection device is arranged to be movable along a substantially circular course around a support that accommodates the patient. In particular, one laser projector is sufficient in this case, which can be moved on a circular rail above and/or below the support, so that it can reach all the body regions of a patient and represent the figure on the same. The respective holding positions of the projector on the rail required for representing a figure can be determined by the control device or the respective implemented virtual simulation program, and a drive device for moving the projection device can be addressed in a corresponding manner.

The apparatus according to the present invention can be suited for the execution of the method according to the present invention in particular. Correspondingly, the method of the invention can be performed with the apparatus of the invention.

BRIEF DESCRIPTION OF EACH OF THE
FIGURES OF THE DRAWINGS

Figure 2:
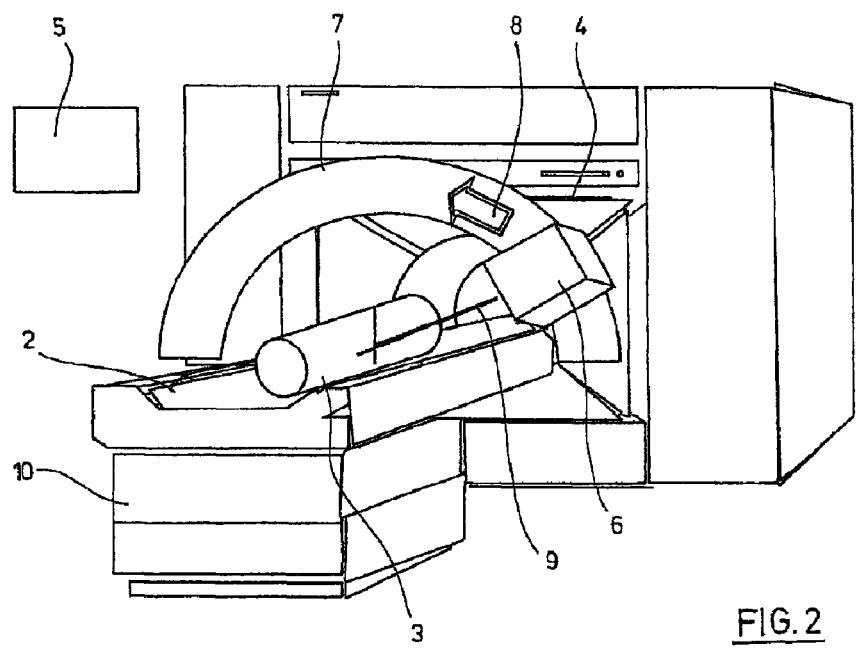
Figure 3:
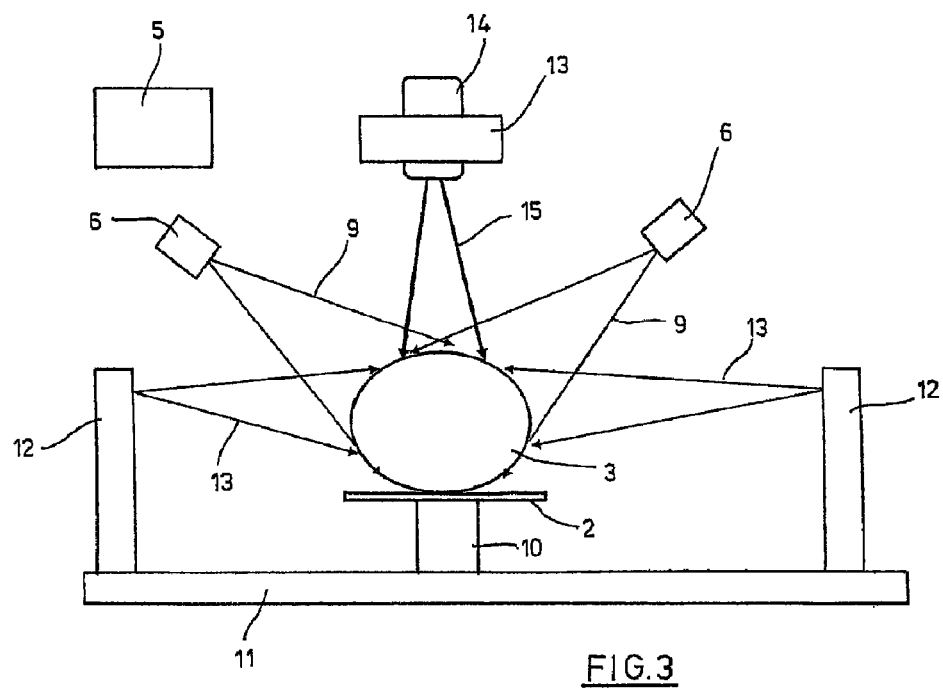
Figure 4:
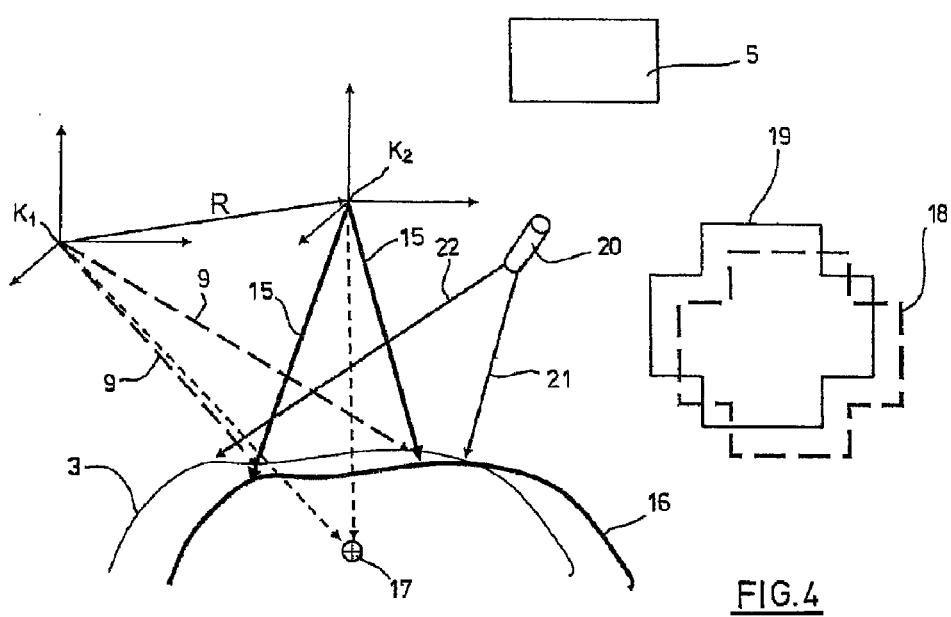

An example of the realisation of the invention will be explained in more detail in the following by means of drawings. Schematically shows:

FIG. 1 an apparatus of the present invention according to a first embodiment,

FIG. 2 an apparatus of the present invention according to a second embodiment,

FIG. 3 an apparatus of the present invention according to a third embodiment, and FIG. 4 a schematic representation for illustrating the functionality of the apparatus of the present invention.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated As far as not indicated otherwise, same reference signs indicate same objects in the figures. In FIG. 1, an apparatus 1 of the invention for the representation of a geometrical figure on the surface of a patient's body is depicted. The apparatus has a support 2, mounted adjustably along at least three axes by means of adjustment drives not shown in more detail, a CT table 2 in the example. On the CT table 2, a body 3, a patient's body 3 for instance, is depicted in a very schematic manner. Further, the apparatus 1 comprises a computer tomography machine 4 arranged in a housing. In this CT machine 4, CT recordings and a three dimensional sectional image of a patient based on these can be made in a per se known manner. Thereafter, a detection of the target volumes for the irradiation with ionising radiation takes place in the frame of an irradiation planning. In a control device 5, the coordinates of a corresponding desired intersection area of a therapy area on the surface of the patient's body 3 envisioned for the radiation therapy are calculated on the basis of target volumes established by the 3D sectional image of the patient.

The apparatus depicted in FIG. 1 comprises two projection devices 6 each having a laser. In this, the projection devices 6 are arranged stationarily in the room that accommodates the apparatus and provided in such an angle to the patient's body that all the regions of the patient's body 3 can be reached commonly by the lasers of the projection devices 6. A given geometrical figure is projected onto the surface of the patient body 3 by at least one of the projection devices 6, while a laser beam 9 generated by the laser is guided sufficiently rapidly along the geometrical figure, so that the impression of a closed contour results for a human observer. The laser beam 9 is guided along the figure via two electrically driven galvanometer mirrors.

In FIG. 2, a further embodiment of the apparatus of the present invention is depicted. The same differs from that one of FIG. 1 only in that instead of two stationarily arranged projection devices 6, only one projection device 6 is provided which can be moved by means of adjustment drives, not shown in more detail, along a circular rail 7 running above the treatment table 2, as is schematically indicated by the arrow 8. In this, the respective holding position of the projection device 6 along the rail 7 can be selected by the control device 5 depending on the respective desired geometrical figure that is to be represented, and the adjustment drives can be addressed in a corresponding manner. With this embodiment, only one projection device 6 is necessary in order to be able to represent the geometrical figure on the entire surface of the patient's body 3.

In FIG. 3, an apparatus of the present invention according to a further embodiment is depicted. According to this embodiment, two stationarily arranged projection devices 6 are arranged in the irradiation room used for the radiation therapy, together with the control device 5. Again, a patient's body 3 is shown very schematically on a support 2, which is itself supported on the floor 11 of the treatment room via a pedestal 10. Further, the apparatus in FIG. 3 has two lasers 12, arranged stationarily and opposite to each other on both sides of the patient's body 3. In a per se known manner, the same serve for positioning the patient's body 3 on the support 2 by means of marks arranged on the patient's body 3. Subsequently, a control of the support 2 takes place such that the patient's body 3 is moved into the given position occupied during the radiation treatment.

Alternatively or in addition to the lasers 12, a laser scanning system 13, depicted only schematically in FIG. 3, or another system for acquiring the body surface may also be provided. Such a system is offered by the applicant under the name "Galaxy" for instance.

Furthermore, the apparatus depicted in FIG. 3 comprises an irradiation machine 14, in the present case a linear accelerator (LINAC). The irradiation machine 14 generates an ionising radiation for tumour treatment in the patient's body 3. In the apparatus according to FIG. 3, again by a projection device, the given geometrical figure is projected with laser radiation 9 to the patient's body 3. In this, the projection of the figure takes place like already described referring to FIGS. 1 and 2. At the same time, a light radiation 15 corresponding to the ionising radiation generated by the irradiation machine is generated by the irradiation machine 14. This light radiation 15 generates a light intersection area on the patient's body 3. The geometrical figure can be a desired intersection area of the ionising radiation of the irradiation machine 14 with the patient's surface. In this case, the light intersection area that corresponds to the area of intersection of the ionizing radiation to be generated by the irradiation machine 14 with the patient's surface must be brought into overlapping with the geometrical figure. By a comparison of the figure projected to the patient's body surface by the projection device 6 with the light intersection area generated by the irradiation machine 14, the correct alignment of the patient can now be checked. However, a prerequisite for this is that the patient is positioned exactly as in the previous CT mapping. The check of this positioning will be explained in more detail in the following.

Even though this is not shown in FIGS. 1 to 3, the apparatuses shown there each still have a sensor device 20, which is shown in FIG. 4 for instance. The sensor device 20 has one or preferably several cameras, by which the geometrical figure projected onto the patient's surface 3 by each of the projection device(s) 6 is recorded. The field of vision of the camera(s) 20 is schematically indicated by the arrows 21, 22. The acquired data are forwarded from the sensor device 20 to the control device 5, which determines the three-dimensional coordinates of the geometrical figure projected onto the patient's body 3 from them. A three-dimensional mapping of the patient's body 3 had been made before the projection of the geometrical figure onto the patient's body, for instance by means of the CT-device 4 shown in FIGS. 1 and 2. The irradiation planning for a tumour existing in the body was then performed by means of this mapping. In particular, the tumour was located, and at least one desired intersection area of the irradiation machine with the body surface was determined. This desired intersection area was then given as the geometrical figure. Based on this, and with fixedly given arrangement of the projection device(s) 6, the 3D-coordinates of this figure were calculated as a desired intersection area on the virtual body surface by the control device 5. These coordinates were preset as desired coordinates by the control device 5. That is to say, the position of the patient's body in the CT-mapping serves as the reference position. The coordinates of the desired intersection area determined by the control device 5 and really projected onto the body 3 are then compared with the desired coordinates.

Regarding this, in FIG. 4 it can still be recognised that different coordinate systems K1, K2 are valid for the projection device 6 and the irradiation machine 14. Their points of origin can be transformed into each other via a transformation vector R. In the example depicted in FIG. 4, the real patient's body 3 is distant from a reference position 16 of the patient's body 3. The isocentre for the irradiation is shown at 17 for the desired position 16 of the patient's body 3. Due to the deviation of the real patient's body 3 from the reference position 16, the desired intersection area 18 projected by the projection device 6 onto the patient's body 3 and the virtual intersection area 19 on the virtual patient's body are not coincident, as is shown schematically in FIG. 4. In order to correct this deviation, for instance the support 2 or its adjustment drives can be controlled such as to bring the patient's body into the correct position, namely into the reference position.

In this it is also possible that the geometrical figure projected onto the patient's body 3 is captured several times per second by the sensor device 20, and the respective measurement data are forwarded to the control device 5. From these, the latter can determine the 3D-coordinates of the projected figure, again several times per second, essentially in real time, and compare them with the desired coordinates. Just when the geometrical figure is projected onto the patient's body in the region of the thorax, monitoring the breathing cycle of the patient is possible in this way. Correspondingly, for instance the irradiation machine can then be activated only at a certain position of the thorax, that is to say in a certain position of the breathing cycle, and otherwise it can be deactivated. By this gating, it is ensured that even at a position change of the organs by breathing, and by this possibly also of the tumour, the desired portions of the body are irradiated at any time.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An apparatus for the representation of a geometrical figure on the surface of a patient's body that is situated on a support, comprising: at least one projection device (6), by which a given geometrical figure can be projected onto the three-dimensional surface of the patient's body (3), at least one control device (5) and at least one optical sensor device (20), by which the geometrical figure projected onto the surface of the patient's body (3) can be acquired and the acquired data can be supplied to the control device (5), wherein the control device (5) is realized to determine the three-dimensional coordinates of the geometrical figure projected onto the patient's body from the data acquired by the sensor device (20), and wherein the control device (5) is realized to compare the determined three-dimensional coordinates of the geometrical figure projected onto the patient's body with desired three-dimensional coordinates, further characterized in that the sensor device (20) is realized to produce a mapping of the geometrical figure several times per second and to supply the acquired data to the control device (5), and that the control device (5) is realized to determine the three-dimensional coordinates of the geometrical figure projected onto the patient's body (3) from the mapping data several times per second and to compare them with the desired coordinates also several times per second.

2. An apparatus according to claim 1, characterized in that the projection device (6) has at least one light source, at least one laser in particular, wherein the geometrical figure can be projected onto the surface of the patient's body (3) while at least one light beam (9) generated by the light source, at least one laser beam (9) generated by the laser in particular, can be guided along the coordinates sufficiently rapidly, so that the impression of a closed contour along the coordinates results.

3. An apparatus according to claim 1, characterized in that the desired coordinates were determined in the frame of an irradiation planning or virtual simulation, in which a virtual representation of at least the surface of the patient's body (3) had been produced, wherein the desired coordinates are those coordinates of the geometrical figure that would result if the projection device (6) would project the geometrical figure onto the virtual patient's body.

4. An apparatus according to claim 1, characterized in that the apparatus has a visualization software, by which the coordinates of the given geometrical figure and the figure resulting from them as well as the desired coordinates and the desired figure resulting from them can be displayed, preferably displayed in different views.

5. An apparatus according to claim 1, characterized in that from the comparison of the determined coordinates and the desired coordinates, a displacement vector for the support (2) can be calculated by the control device (5) in order to bring the determined coordinates into coincidence with the desired coordinates.

6. An apparatus according to claim 5, characterized in that the support (2) is movable along one or plural degrees of freedom by means of suitable adjustment drives, and the control device (5) is realized to control the adjustment drives such that the support (2) is moved according to the calculated displacement vector.

7. An apparatus according to claim 5, characterized in that the control device (5) is realized to calculate the displacement vector several times per second, and to control the adjustment drives such that the support (2) is moved according to the calculated displacement vector.

8. An apparatus according to claim 1, characterized in that it has an irradiation machine (14) for generating ionizing radiation for a radiation therapy of the patient's body, and that the control device (5) is realized to control the irradiation machine (14) several times per second to generate the ionizing radiation always then when the comparison of determined coordinates and desired coordinates takes on a desired value.

9. A method for the representation of a geometrical figure on the surface of a patient's body that is situated on a support, comprising the steps: a given geometrical figure is projected onto the three-dimensional surface of the patient's body (3) by a projection device (6), the geometrical figure projected onto the surface of the patient's body (3) is acquired by means of an optical sensor device (20) and the acquired data are supplied to a control device (5), wherein the control device (5) determines the three-dimensional coordinates of the geometrical figure projected onto the patient's body from the data acquired by the sensor device (20), the determined three-dimensional coordinates of the geometrical figure projected onto the patient's body are compared with desired three-dimensional coordinates by the control device, further characterized in that the sensor device (20) produces a mapping of the geometrical figure several times per second and supplies the acquired data to the control device (5), and that the control device (5) determines the three-dimensional coordinates of the geometrical figure projected onto the patient's body (3) several times per second and compares them with the desired coordinates also several times per second.

10. A method according to claim 9, characterized in that the geometrical figure is projected onto the surface of the patient's body (3) while at least one light beam (9), at least one laser beam (9) in particular, is guided along the coordinates sufficiently rapidly, so that the impression of a closed contour along the coordinates results.

11. A method according to claim 9, characterized in that the desired coordinates are determined beforehand in the frame of an irradiation planning or virtual simulation, in which a virtual representation of at least the surface of the patient's body (3) is produced, wherein those coordinates of the geometrical figure are given as the desired coordinates that would result if the projection device (6) would project the geometrical figure onto the virtual patient's body.

12. A method according to claim 9, characterized in that the coordinates of the given geometrical figure and the figure resulting from them as well as the desired coordinates and the desired figure resulting from them are displayed by a visualization software, preferably displayed in different views.

13. A method according to claim 12, characterized in that based on the representation of the coordinates of the given geometrical figure and the figure resulting from the same, as well as on the desired coordinates and the desired figure resulting from the same, both figures are brought into coincidence in the representation by the visualization software, and by iterative movement of the support in particular.

14. A method according to claim 9, characterized in that from the comparison of the determined coordinates and the desired coordinates, a displacement vector for the support (2) is calculated in order to bring the determined coordinates into coincidence with the desired coordinates.

15. A method according to claim 14, characterized in that the support (2) is movable along one or plural degrees of freedom, and the control device (5) controls the adjustment drives such that the support (2) is moved according to the calculated displacement vector.

16. A method according to claim 14, characterized in that the control device (5) calculates the displacement vector several times per second, and controls the adjustment drives such that the support (2) is moved according to the calculated displacement vector.

17. A method according to claim 9, characterized in that it has an irradiation machine (14) for generating ionizing radiation for a radiation therapy of the patient's body (3), and that the control device (5) controls the irradiation machine (14) several times per second to generate the ionizing radiation always then when the comparison of determined coordinates and desired coordinates takes on a desired value.

* * * * *